(12) United States Patent
Liu et al.

(10) Patent No.: US 11,285,282 B2
(45) Date of Patent: Mar. 29, 2022

(54) RESPIRATOR AND METHOD FOR PROCESSING THE RESPIRATOR, CONTROL SYSTEM, PROGRAM AND READABLE CODES

(71) Applicant: BMC Medical Co., Ltd., Beijing (CN)

(72) Inventors: Lijun Liu, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 316 days.

(21) Appl. No.: 15/744,799

(22) PCT Filed: Jan. 18, 2017

(86) PCT No.: PCT/CN2017/071565
§ 371 (c)(1),
(2) Date: Jan. 14, 2018

(87) PCT Pub. No.: WO2017/129019
PCT Pub. Date: Aug. 3, 2017

(65) Prior Publication Data
US 2018/0200463 A1 Jul. 19, 2018

(30) Foreign Application Priority Data
Jan. 26, 2016 (CN) .......................... 201610053169.2

(51) Int. Cl.
*A61M 16/00* (2006.01)

(52) U.S. Cl.
CPC ...... *A61M 16/024* (2017.08); *A61M 16/0066* (2013.01); *A61M 16/0069* (2014.02);
(Continued)

(58) Field of Classification Search
CPC .... A61M 16/021–024; A61M 16/0069; A61M 16/0066; A61M 2205/0216;
(Continued)

(56) References Cited

U.S. PATENT DOCUMENTS

2005/0103339 A1* 5/2005 Daly ..................... F04D 27/004
128/204.18
2009/0120446 A1* 5/2009 Vaska ..................... A61F 5/566
128/848
(Continued)

FOREIGN PATENT DOCUMENTS

CN 2198424 Y 5/1995
CN 1761498 A 4/2006
(Continued)

*Primary Examiner* — Elliot S Ruddie
(74) *Attorney, Agent, or Firm* — Bayramoglu Law Offices LLC

(57) ABSTRACT

Disclosed are a respirator and a handling method, a control system, a program and a readable medium thereof. The respirator comprises blowers and an airflow output channel which communicates with the corresponding one of the blowers. The blowers include a first blower and a second blower; an air inlet of the second blower communicates with an air outlet of the first blower, and an air outlet of the second blower communicates with the airflow output channel. The respirator of the disclosure adopts a power structure which includes the first blower and the second blower, wherein the first blower as an air supply source supplies air to the second blower to obtain a two-level pressure boosting effect.

15 Claims, 9 Drawing Sheets

(52) U.S. Cl.
CPC ............... *A61M 2205/0216* (2013.01); *A61M 2205/3365* (2013.01); *A61M 2205/42* (2013.01); *A61M 2205/502* (2013.01); *A61M 2205/52* (2013.01)

(58) Field of Classification Search
CPC ...... A61M 2205/33; A61M 2205/3365; A61M 2205/42; A61M 2205/50; A61M 2205/502; A61M 2205/52; A61M 16/0057; A61M 16/06; A61M 16/0875; A61M 16/107; A61M 2205/82; F04D 17/122; F04D 17/125; F04D 25/06; F04D 25/166; F04D 27/004; F04D 29/281; F04D 29/284; F04D 29/4213; F04D 29/4226; F04D 29/661; F04D 29/663; F04D 17/12; F04D 25/16; F04D 29/403; F04D 29/424; F04D 29/441; F04D 13/12; F04D 17/08; F04D 27/0261; F04D 15/00; F04D 15/0066; F04D 17/00–18; F04D 19/007; F04D 19/02; F04D 19/026

See application file for complete search history.

(56) References Cited

U.S. PATENT DOCUMENTS

| | | | | |
|---|---|---|---|---|
| 2012/0328969 | A1* | 12/2012 | DeWald | H01M 8/04082 |
| | | | | 429/455 |
| 2013/0228181 | A1* | 9/2013 | Ahmad | A61M 16/0069 |
| | | | | 128/204.23 |
| 2014/0227091 | A1* | 8/2014 | Kenyon | A61M 16/0057 |
| | | | | 415/199.2 |
| 2014/0323030 | A1* | 10/2014 | Rugge | F24F 11/74 |
| | | | | 454/256 |

FOREIGN PATENT DOCUMENTS

| | | |
|---|---|---|
| CN | 1805766 A | 7/2006 |
| CN | 105597208 A | 5/2016 |
| CN | 205515850 U | 8/2016 |
| DE | 102014009895 A1 | 1/2015 |

\* cited by examiner

RESPIRATOR AND METHOD FOR PROCESSING THE RESPIRATOR, CONTROL SYSTEM, PROGRAM AND READABLE CODES

CROSS-REFERENCE TO RELATED APPLICATIONS

This application is the national stage of International Application No. PCT/CN2017/071565 filed Jan. 18, 2017, which claims the benefit of Chinese Patent Application No. CN201610053169.2, filed Jan. 26, 2016, the entirety of which are incorporated herein by reference.

FIELD OF TECHNOLOGY

The disclosure relates to the technical field of positive pressure ventilation therapeutic machines and, more specifically, to a respirator, a control system of the respirator, a method for processing the respirator, a program and a readable medium.

BACKGROUND

Consumer requirements on the performance of household respirators become higher and higher along with the popularization of the respirators, in particular the performance in the aspects of noise, response speed, heat value, power supply, volume, etc. of the respirators. The respirator usually consists of a main machine, a mask and a conduit. The main machine is internally provided with blowers; an air outlet of one of the blowers is connected to one end of the conduit, and the other end of the conduit is connected with the mask. The blowers in the main machine can output air with pressure to supply air to a patient. Household respirators currently available in the market usually adopt a blower structure as a power source. The power structure has the problem that excessive load generated at a high temperature results in a decline in the performance of the respirator, which is mainly reflected in the following way: when a high pressure is required, the rotating speeds of the blowers rise, and then a lot of heat is generated that affect the performance of the blowers; when the blowers work at a high pressure, the rise of the rotating speed is relatively slow, it fails to reach a designated pressure value in time; when the blowers work at a high rotating speed, vibration and noise increase, seriously affecting the use experience of consumers.

SUMMARY

One objective of the embodiments of the disclosure is to provide a respirator to improve the performance of the respirator at a high pressure and to solve the problems of slow rise of the blower speed and loud noise of the respirator.

To solve the problem, the present disclosure discloses a respirator, comprising blowers and an airflow output channel (4) which communicates with the corresponding one of the blowers, wherein the blowers include a first blower and at least one second blower; an air inlet of the second blower communicates with an air outlet of the first blower, and an air outlet of the second blower communicates with the airflow output channel.

Preferably, the respirator also comprises a sealing housing which is located on the exterior of the second blower and encloses the second blower, and a space is formed between the sealing housing and the second blower to form a heat dissipating cavity for air flow; the air outlet of the first blower communicates with a cavity inlet of the heat dissipating cavity, and the air inlet of the second blower communicates with the air outlet of the first blower through the cavity inlet.

Preferably, the air inlet of the second blower is back to the cavity inlet of the heat dissipating cavity; or, a central line of the air inlet of the second blower is not super-imposed with a central line of the cavity inlet of the heat dissipating cavity.

Preferably, the blowers include at least two second blowers, and the second blowers are connected in a sequence series in a way that the air outlet of the previous second blower communicates with the air inlet of the next second blower.

Preferably, the air inlet of each one of the second blowers communicates with the air outlet of the first blower through a sealing pipe.

Preferably, the sealing connection between the sealing pipe and the air inlet of the second blower, and the sealing connection between the sealing pipe and the air outlet of the first blower are achieved through a sealing material; or, the sealing connection between the sealing pipe and the air inlet of the second blowers, and the sealing connection between the sealing pipe and the air outlet of the first blower are achieved through a conical surface connecting structure.

Preferably, the first blowers and the second blowers are configured in a one-to-one correspondence way; the air outlet of the first blower is in a sealing connection with the air inlet of the second blowers through an elastic sealing member, wherein the first blowers and the second blowers are fixedly installed at a blower fixing cabin.

Preferably, the first blowers and the second blowers are configured in a one-to-one correspondence way; the air outlet of the first blower is in a sealing connection with the air inlet of the second blower through an elastic sealing bag, wherein the first blower and the second blower are enclosed in the elastic sealing bag, the air outlet of the first blower and the air inlet of the second blower communicate with each other in each corresponding elastic sealing bag, and the air inlet of the first blower and the air outlet of the second blower are exposed through each corresponding elastic sealing bag.

To solve the problem above, the present disclosure further discloses a control system of a respirator, wherein the respirator is the respirator according to embodiments of the present disclosure; the control system comprises:

an input unit, configured to receive a preset target output pressure;

a control unit, configured to determine rotating speeds of the first blower and the second blower according to the target output pressure provided by the input unit, and driving the first blower and the second blower to run according to the determined rotating speeds.

Preferably, the control system further comprises:

a monitoring unit configured to monitor an actual output pressure of the airflow output channel in the respirator.

Preferably, the control system further comprises:

a display unit, configured to display the actual output pressure provided by the monitoring unit.

Preferably, the input unit is further configured to receive a rotating speed adjusting requests, and send the rotating speed adjusting requests to the control unit, wherein the rotating speed adjusting requests comprise a rotating speed rise request and a rotating speed reduction request;

the control unit is further configured to receive the rotating speed adjusting request provided by the input unit and adjust the rotating speeds of the blowers according to the rotating speed adjusting requests.

Preferably, the control unit comprises: a first control sub-unit, configured to determine the rotating speed of the first blower and drive the first blower to run according to the determined rotating speed; and a second control sub-unit, configured to determine the rotating speed of the second blower and drive the second blower to run according to the determined rotating speed.

To solve the problem above, the present disclosure further discloses a method for processing a respirator, wherein the respirator is the respirator according to the embodiments of the present disclosure; the method comprises:

receiving a preset target output pressure by the respirator;

determining rotating speeds of the first blower and the second blower according to the target output pressure, and driving the first blower and the second blower to run according to the determined rotating speeds.

Preferably, the method further comprises:

monitoring an actual output pressure of the airflow output channel which communicates with the second blower, and displaying the actual output pressure.

Preferably, the method further comprises:

receiving a rotating speed adjusting request by the respirator;

adjusting the rotating speeds of the blowers according to the rotating speed adjusting request, wherein the blowers include the first blower and the second blower.

Preferably, the rotating speed adjusting request includes a rotating speed rise request and a rotating speed reduction request, wherein the step of adjusting the rotating speeds of the blowers according to the rotating speed adjusting request comprises: increasing the rotating speed of each one of the blowers by an adjusting step each time when receiving the rotating speed rise request; or reducing the rotating speed of each one of the blowers by an adjusting step each time when receiving the rotating speed reduction request.

Increasing the rotating speed of each one of the blowers by an adjusting step each time when receiving the rotating speed rise request; or reducing the rotating speed of each one of the blowers by an adjusting step each time when receiving the rotating speed reduction request. Wherein the blowers include the first blower and the second blower.

To solve the problem above, the present disclosure further discloses program, comprising readable codes, wherein when the readable codes are running in a device, the device executes the method for processing a respirator according to embodiments of the present disclosure.

To solve the problem above, the present disclosure further discloses a readable medium, storing the program according to embodiments of the present disclosure.

A beneficial effect of the disclosure is as follows. The respirator of the disclosure adopts a power structure which includes the first blower and the second blower, wherein the first blower as an air supply source supplies air to the second blower to obtain a secondary pressure boosting effect. Therefore, with respect to the existing respirators (which adopt a single-blower power structure), the respirator of the disclosure may lower the requirements for the rotating speeds of the blowers under the condition of the same target output pressure, and then the respirator of the disclosure has higher performance in the aspects of response speed, noise reduction, heat value, air supply, etc.

Through a detailed description of the illustrative embodiments of the disclosure with reference to the drawings below, the characteristics and advantages of the disclosure will be clearer.

BRIEF DESCRIPTION OF THE DRAWINGS

Attached drawings, incorporated in the description as part of the description, illustrate embodiments of the disclosure, and together with the explanations thereof present the principle of the disclosure.

Figure 1:
FIG. 1 is a block diagram showing the principle of blowers of a respirator according to one embodiment of the disclosure.
Figure 2:
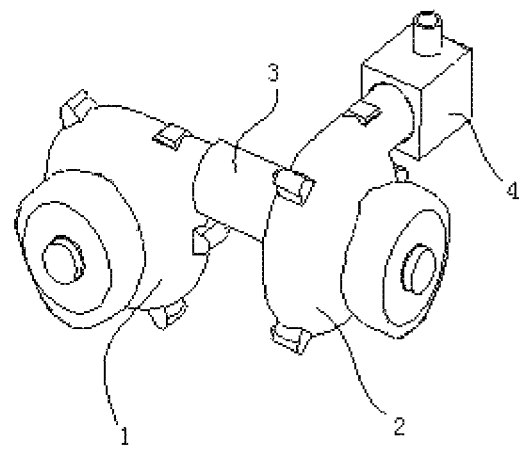
FIG. 2 is a structural schematic diagram showing the blowers of a respirator according to one embodiment of the disclosure.
Figure 3:
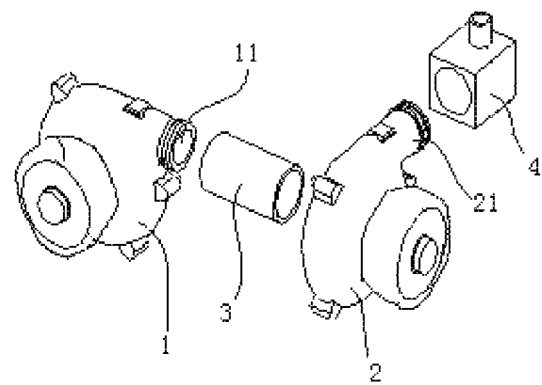
FIG. 3 is an exploded diagram of a blower as shown in FIG. 2.

| Description of the numbers in the attached drawings: | |
| --- | --- |
| 1-First blower | 11-Air outlet of the first blower |
| 2-Second blower | 21-Air outlet of the second blower |
| 22-Air inlet of the second blower | 3-Sealing pipe |
| 4-Airflow output channel; | 51-Input unit |
| 52-Control unit | 53-Monitoring unit |
| 54-Display unit | 6-Blower fixed cabin |
| 7-Elastic sealing member | 8-Elastic sealing bag |
| 81-Rib position; | 9-Sealing housing; |
| 91-Heat dissipating cavity; | 92-Neck portion; |
| 91a-Cavity inlet | 93-Connection opening. |

DETAILED DESCRIPTION OF THE EMBODIMENTS

The illustrative embodiments of the disclosure are described in detail below with reference to the attached drawings. It should be noted that, unless otherwise specified, the relative arrangements, digital expression forms and numerical values of the parts and steps described in the embodiments are not limited to the scope of the disclosure.

The description of at least one illustrative embodiment below is actually merely illustrative, and never imposes any limit to the disclosure and applications or use thereof.

Technologies, methods and devices known by those ordinarily skilled in the art may be not discussed in detail, but under proper circumstances, the technologies, methods and devices should be deemed as a part of the Description.

In all examples illustrated and discussed here, any specific values should be interpreted to be illustrative instead of limiting. Therefore, other examples of the illustrative embodiments may have different values.

It should be noted that similar marks and letters in the following drawings represent similar items, so once a certain item is defined in a drawing, the item is not discussed in further detail in the subsequent drawings.

In order to solve the problem of the power structure of the existing respirator that the excessive load at a high pressure results in a decline in the performance of the respirator, the disclosure provides an improved respirator. As shown in FIG. 1 to FIG. 10, the respirator of the disclosure includes blowers and an airflow output channel 4 which communicates with a corresponding one of the blowers, and blowers include a first blower 1, and a second blower 2 corresponding to the first blower 1. Herein, one first blower 1 may correspond to one second blower 2, or two or more second blowers 2; when the blowers of the respirator include at least two second blowers, which means a plurality of second blowers 2 exist, the plurality of second blowers 2 can be connected together by means of a series connection, and the series connection specially refers to that an air outlet 21 of a previous second blower 2 is connected with an air inlet of the next second blower 2. The first blower 1 and/or the second blowers 2 may be any one of various types of blowers such as centrifugal blowers and axial flow blowers. This embodiment of the disclosure has no specific limits as to the types of the blowers. The plurality of the second blowers 2 in a series connection may be blowers of different types and different functions. This embodiment of the disclosure has no specific limits in the types and functions of the second blowers.

In the disclosure, FIG. 1-10 illustrate an embodiment with one first blower 1 and one second blower 2, wherein an air inlet 22 of the second blower 2 communicates with an air outlet 11 of the corresponding first blower 1, and an air outlet 21 of the second blower 2 communicates with an airflow output channel 4, which means that the respirator finally supplies air to a patient via the airflow output channel 4. The airflow output channel may be the conduit of the respirator or a part of the conduit of the second blower 2 or other parts which lead the air generated by the second blower out.

The respirator in the disclosure adopts a power structure which has the first blower 1 and the second blower 2, wherein the first blower 1 as a power supply source supplies air to the second blower 2, so the power structure can obtain a two-level boosting effect. Therefore, with respect to the existing respirators (which adopt a single-blower power structure), the respirator of the disclosure may lower the requirements for the rotating speeds of the blowers under the condition of the same target output pressure, and then the respirator of the disclosure has higher performance in the aspects of response speed, noise reduction, heat value, air supply, etc. For example, under the condition that the target output pressure is 20 hpa, the target rotating speed of the blower of the existing respirator has to reach 25,000 rpm (round/minute), and the response time (namely the time required to increase the rotating speed from the initial value, namely 0 rpm, to the target rotating speed, namely 25,000 rpm) is 13.375 s; under the condition that the respirator of the disclosure adopts the power structure which has one first blower 1 and one second blower 2, if the performance of the first blower 1 and the second blower 2 is identical with that of the blower of the existing respirator, then the target rotating speeds of the first blower 1 and the second blower 2 of the respirator of the disclosure are reduced to 18,000 rpm, and the response time is reduced to 13.215 s. Thus it can be seen that, with respect to the existing respirators, the respirator of the disclosure has a higher response speed under the condition of the same target output pressure and the blowers of the respirator of the disclosure have obviously lower rotating speeds than the rotating speed of the blower of the existing respirator. Therefore, with respect to the existing respirators, the respirator of the disclosure has lower noises and lower heat values under the condition of the same target output pressure. From another perspective, in comparison with the existing respirators, the respirator of the disclosure obtains a bigger air supply under the condition of identical response speeds, identical heat values and identical noise levels.

In order to further enhance the effects of the blowers in the respirator of the disclosure, the air outlet 11 of the first blower 1 should be in a sealing connection with the air inlet 22 of the corresponding second blower 2 such that the air discharged from the first blower 1 can be completely transferred to the corresponding second blower 2, thus enhancing the utilization rate of the blowers. Below are several optional sealing connecting structures.

A first sealing connection structure: In one embodiment of the disclosure, as shown in FIG. 2 to FIG. 6, the air inlet 22 of the second blower 2 communicates with the air outlet 11 of the first blower 1 through a sealing pipe 3, wherein the sealing pipe 3 is in a sealing connection with the air inlet 22 of the corresponding second blower 2 and the air outlet 11 of the corresponding first blower 1. In this way, the pressurized air may only be output via the airflow output channel 4, thus improving the effects of the blowers. On the above basis, the sealing pipe 3 may be a straight pipe or a bent pipe, and the sealing pipe 3 may have different branches according to the corresponding relationship between the first blower 1 and the second blower 2. In the embodiment as shown in FIG. 2-6, one first blower 1 corresponds to one second blower, and the sealing pipe 3 is a straight pipe without branch channels, which means that the sealing pipe 3 has a single axial direction, thus further enhancing the response speed of the respirator.

In a specific embodiment of the disclosure, the sealing pipes 3 is in a sealing connection with the air inlet 22 of the corresponding the second blower 2 and the air outlet 11 of the corresponding first blower 1 through sealing materials; the sealing materials may be a sealing ring, a sealing rubber, a sealing gasket, etc.; or the sealing pipe 3 is in a sealing connection with the air inlet 22 of each corresponding one of the second blowers 2 and the air outlet 11 of each corresponding one of the first blowers 1 through a conical surface connection structure, wherein the conical surface connection structure includes two conical contact surfaces which form a sealing pair.

Figure 4:
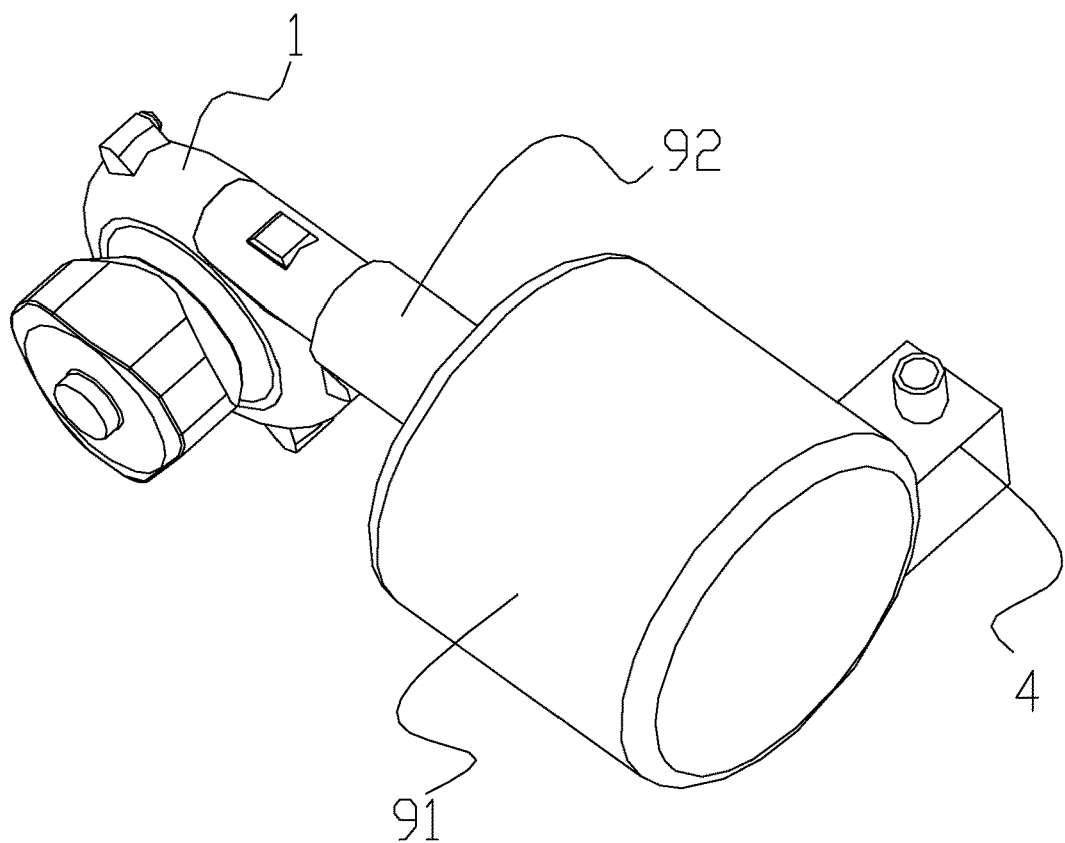
FIG. 4 is a structural schematic diagram showing the blowers of the respirator according to another embodiment of the disclosure.
Figure 5:
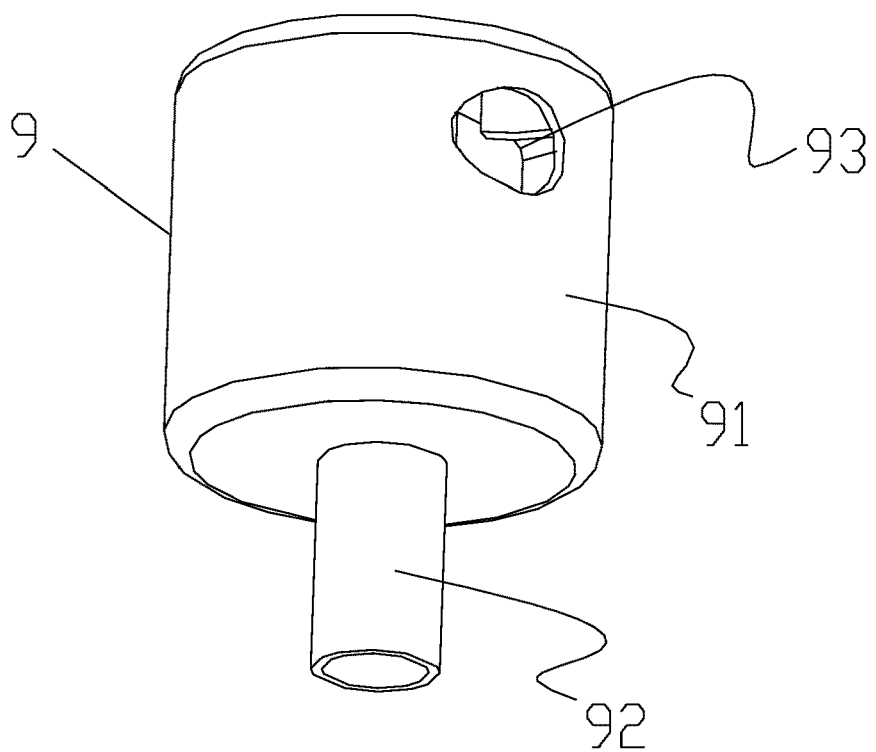
FIG. 5 is a structural schematic diagram of a sealing pipe as shown in FIG. 4.
Figure 6:
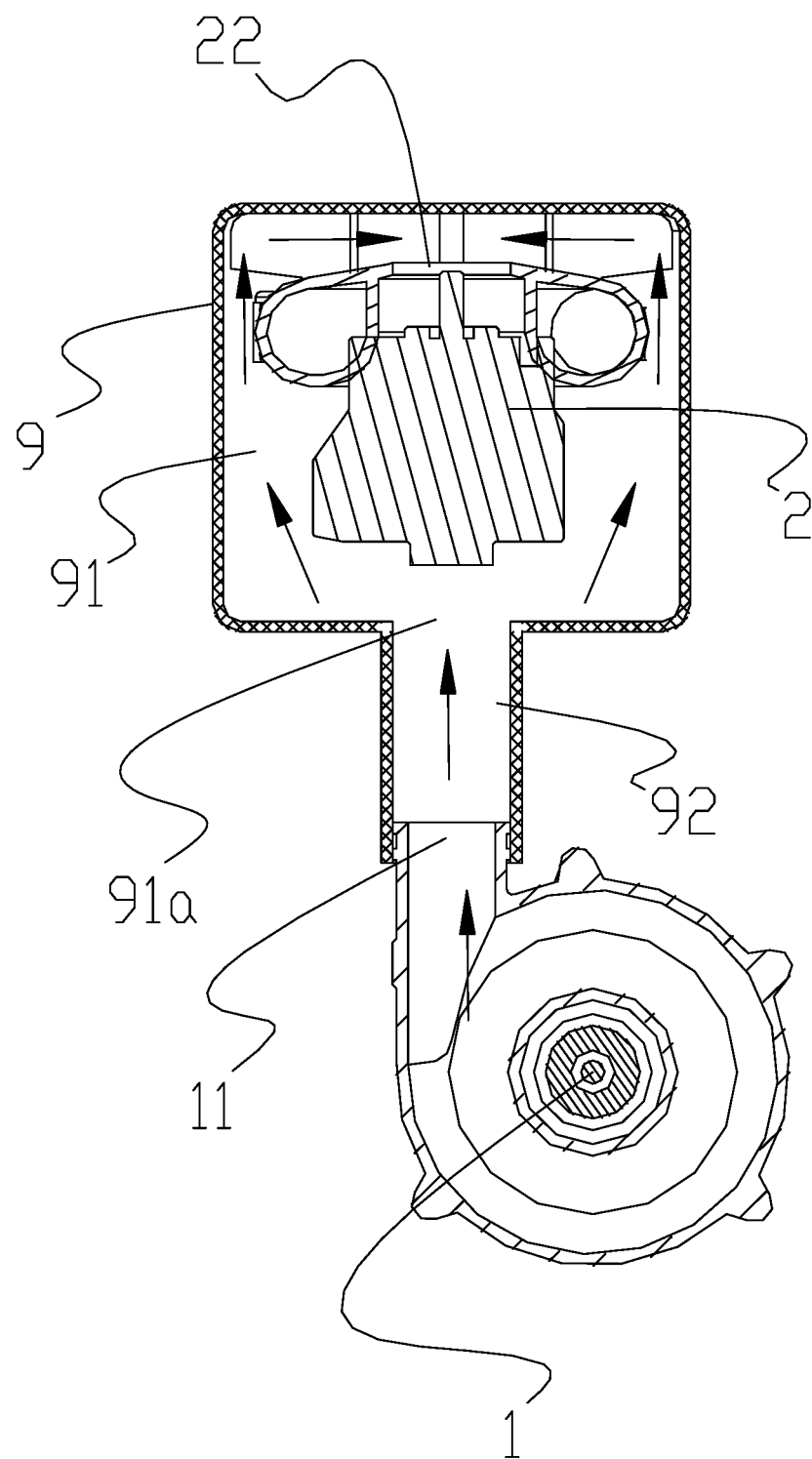
FIG. 6 is a sectional schematic diagram of the blowers as shown in FIG. 4, wherein the arrow in the figure represents the flow direction of air in the sealing pipe.

In order to enhance the heat dissipating capability of the respirator of the disclosure, in a specific embodiment of the disclosure, as shown in FIG. 4 to FIG. 6, on the basis of the above embodiments, a sealing housing 9 which is disposed on the exterior of the second blower 2 and encloses the second blower 2 is also included; space is reserved between the sealing housing 9 and the second blower 2 to form a heat dissipating cavity 91 in which the air flows; the air outlet 11 of the first blower 1 communicates with a cavity inlet 91a of the heat dissipating cavity 91 such that the air inlet 22 of the second blower 2 communicates with the air outlet 11 of the first blower 1 through the cavity inlet 91a, and the air outlet 21 of the second blower 2 is positioned on the sealing housing 99 such that the air outlet 21 of the second blower 2 is capable of communicating with the airflow output channel 4. For example, the sealing housing 9 may be in a sealing connection with the housing of the second blower 2 through a connecting opening 93 such that only the air outlet 21 of the second blower 2 is exposed via the sealing housing 9. In addition, the air inlet 22 of the second blower 2 is preferably the cavity inlet 91a which does not face the heat dissipating cavity 91. In this way, the central line of the air inlet 22 is not superimposed with that of the cavity inlet 91a. This means that the air that enters the heat dissipating cavity 91 via the cavity inlet 91a fails to directly enter the air inlet 22 of the second blower 2, but is required to diffuse and flow in the heat dissipating cavity 91 to enter the air inlet 22 of the second blower 2. Therefore, the air entering the heat dissipating cavity 91 flows through the surface of the second blower 2 and brings away heat generated by the second blower 2, thus fulfilling the aim of assisting the corresponding second blower 2 through the first blower 1. Particularly, as shown in FIG. 6, the air inlet 22 of the second blower 2 is back to the cavity inlet 91a of the heat dissipating cavity 91, and then the air entering the heat dissipating cavity 91 forms a circulating flow and enters the air inlet 22 of the second blower 2, thus achieving the optimum heat dissipating effect.

In order to facilitate installation of the second blower 2 in the sealing housing 9, the sealing housing 9 may be made of elastic materials and a support structure is further placed between the sealing housing 9 and the second blower 2 to support the sealing housing 9 with respect to the second blower 2, thus forming the heat dissipating cavity 91 with a relatively large volume, avoiding blockage of the air inlet 22, and ensuring the smoothness of the air flow in the heat dissipating cavity 91.

In the embodiment as shown in FIG. 4 to FIG. 6, the sealing housing 9 communicates with the air inlet 11 of the first blower 1 through a neck portion 92 which reduces inwards with respect to the heat dissipating cavity 91, so the cavity inlet 91a of the heat dissipating cavity 91 has a small cross section area with respect to the heat dissipating cavity 91. In this way, the air that enters the heat dissipating cavity 91 via the cavity inlet 91a needs to be diffused to reach the air inlet 22 of the second blower 2, thus further improving the effect that the first blower 1 assists the second blower 2 to dissipate heat, wherein the connecting portion between the neck portion 92 and the heat dissipating cavity 91 is the cavity inlet 91a of the heat dissipating cavity 91.

Figure 7:
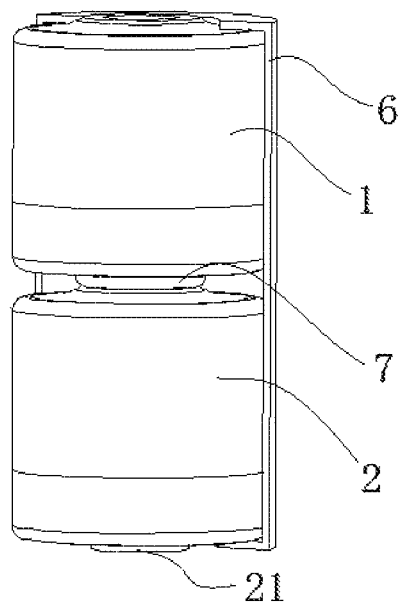
FIG. 7 is a structural diagram showing the principle of the blowers of the respirator according to the third embodiment of the disclosure.
Figure 8:
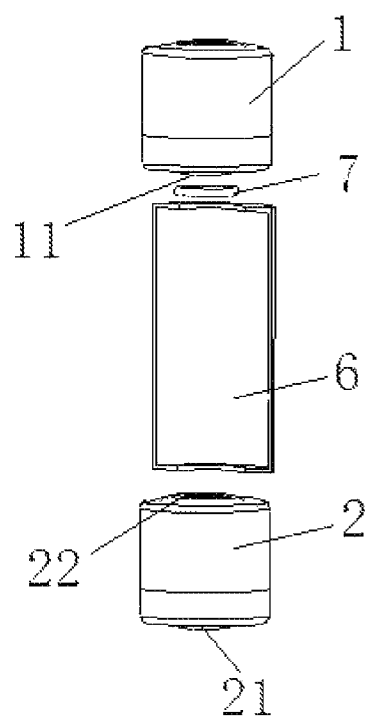
FIG. 8 is an exploded schematic diagram of a blower as shown in FIG. 7.
Figure 9:
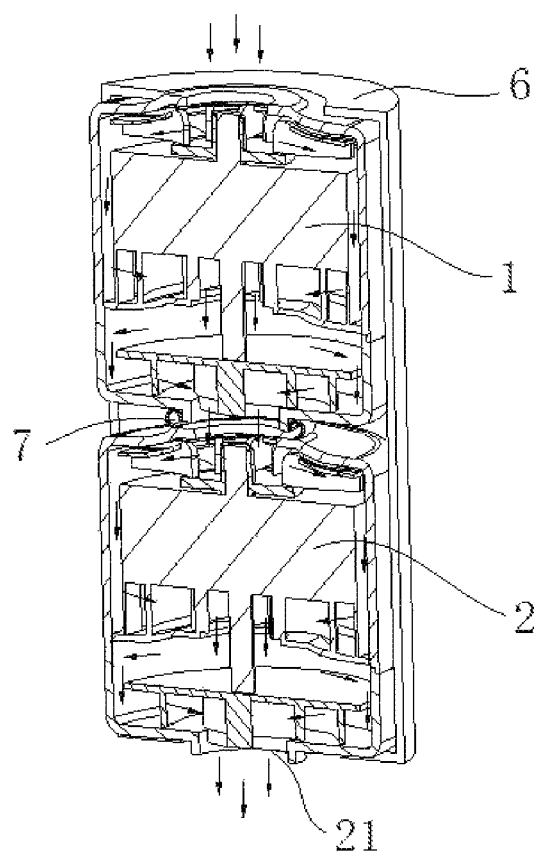
FIG. 9 is a sectional schematic diagram of blowers as shown in FIG. 7, wherein the arrows in the figure represent the flow directions of air in all blowers.

A second sealing connection structure: As shown in FIG. 7 to FIG. 9, in the embodiment in which the first blower 1 and the second bower 2 are configured in a one-by-one correspondence relationship, the air outlet 11 of the first blower 1 is in a sealing connection with the air inlet 22 of the corresponding second blower 2 through a sealing member 7, wherein the first blower 1 and the corresponding second blower 2 are both fixedly installed at a blower fixing cabin 6, and the elastic sealing member 7 is compressed between the first blower 1 and the corresponding second blower 2, thus ensuring the sealing reliability. Therefore, the blower fixed cabin 6 has the role of installing the blowers and keeping the elastic sealing member 7 compressed between the first blower 1 and the corresponding second blower 2.

Herein, the elastic sealing member 7 may be clamped between the edge of the air outlet 11 of the first blower 1 and the edge of the air inlet 22 of the corresponding second blower 2, or clamped between a part of the first blower 1 that is positioned at the outer circumference of the air outlet 11 and a part of the corresponding second blower 2 that is positioned at the outer circumference of the air inlet 22, to form a closed space for enclosing the air outlet 11 and the air inlet 22.

The first blower 1 and the second blower 2 may be fixedly installed at the blower fixing cabin 6 through a flange connection structure or a positioning structure. An example of the positioning structure is as follows: the blower fixing cabin 6 includes an upper stopper portion and lower stopper portion which are arranged with respect to each other and a connecting portion which connects the upper stopper portion and a lower stopper portion together, so that the first blower 1 and the corresponding second blower 2 are connected in a series and then clamped between the upper stopper portion and the lower stopper portion, thus realizing the positioning and fixation of the first blower 1 and the corresponding second blower 2 at the blower fixing cabin 6. Therefore, the upper stopper portion should be provided with an opening through which the air inlet of the first blower 1 is exposed, and the lower stopper portion should be provided with an opening through which the air outlet 21 of the second blower 2 is exposed.

The words "upper", "lower", etc. that represent orientation do not mean to describe the specific positions and orientations of the limited portions, but are merely used for representing the relative position relationships between the limited portions.

In addition, in the embodiment where the first blower 1 and the second blower 2 are fixedly installed at the blower fixing cabin 6 through the positioning structure, in order to facilitate the fixed installation of the first blower 1 and the second blower 2 at the blower fixing cabin 6, the blower fixing cabin 6 may be a split structure wherein the separable parts of the blower fixing cabin 6 can be fixedly connected together through fastening screws.

Figure 10:
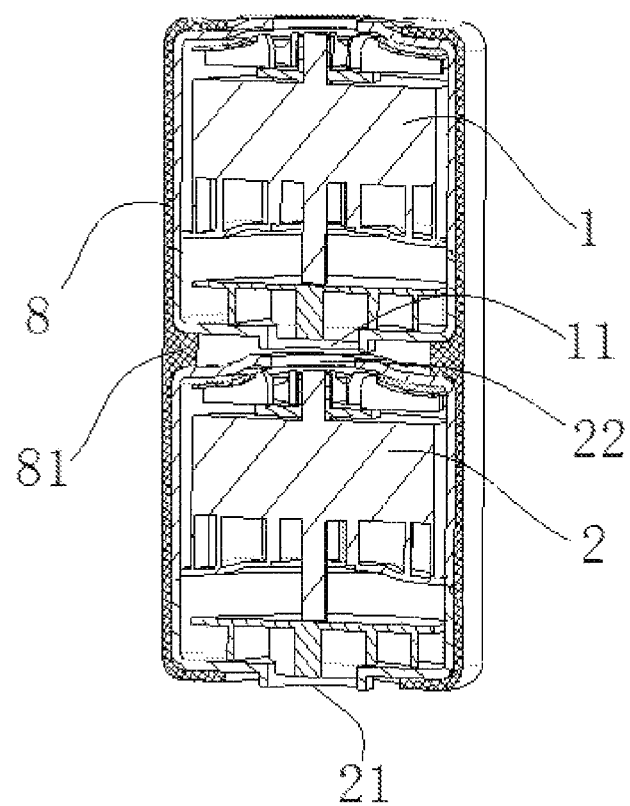
FIG. 10 is a structural diagram showing the principle of the blowers of the respirator according to the fourth embodiment of the disclosure.

A third sealing connection structure: As shown in FIG. 10, in the embodiment where the first blower 1 and the second blower 2 are configured in a one-to-one correspondence relationship, the air outlet 11 of the first blower 1 is also in a sealing connection with the air inlet 22 of the corresponding second blower 2 through an elastic sealing bag 8, wherein both the first blower 1 and the corresponding second blower 2 are tightly enclosed by the elastic sealing bag 8, and the definition of the tight enclosing is that the elastic sealing bag 8 performs elastic deformation when enclosing the first blower 1 and the corresponding second blower 2 such that the elastic sealing bag 8 is tightly hooped on the blower surfaces through the effect of restoring the elastic deformation, thus realizing a sealing connection. Besides, the air outlet 11 of the first blower 1 and the air inlet 22 of the second blower 2 communicate with each other in the formed closed space, while the air inlet of the first blower 1 and the air outlet 21 of the corresponding second blower 2 are both exposed through the elastic sealing bag 8.

The elastic sealing bag 8 may be made of flexible rubber materials, such as silica gel, flexible PVC, EVA (ethylene-vinyl acetate copolymer), POE plastic, etc., to obtain high elastic resilience.

In order to facilitate the positioning of the first blower 1 and the second blower 2 in the elastic sealing bag 8, as shown in FIG. 10, the elastic sealing bag 8 may be provided with rib positions on the inner wall, and the rib positions 81 are clamped between the first blower 1 and the second blower 2 to help position the blowers in the elastic sealing bag 8 through the rib positions 81. In order to improve the positioning effects of the rib positions 81, preferably the elastic sealing bag 8 is provided with a ring of rib positions 81 on the inner wall.

The respirator of the disclosure may control the rotation of the blowers by set adjusting steps, namely rotating speeds of the blowers respectively corresponding to the different pre-set adjusting steps, or may control the rotations of the blowers according to the target output pressure that is input by the user, and the latter is more user-friendly. For this reason, the disclosure also provides a control system capable of executing the control method for controlling the blowers to rotate according to a target output pressure that is input by the user.

Figure 11:
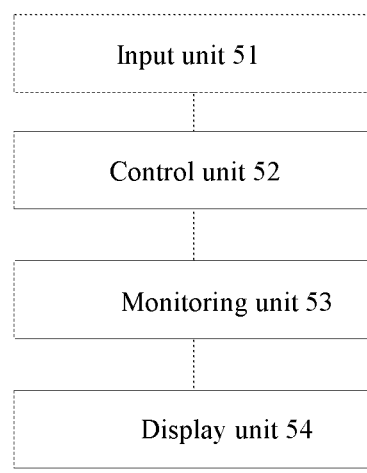
FIG. 11 is a block diagram showing the principle of a control system of the respirator according to one embodiment of the disclosure.

Refer to FIG. 11. FIG. 11 illustrates a block principle diagram of an embodiment of the control system of the respirator of the disclosure. As shown in FIG. 11, the control system may apply to the respirator as described in the above embodiments. Specifically, the control system may include an input unit 51 and a control unit 52.

The input unit 51 may receive a pre-set target output pressure, for example the input unit 51 may include a button and/or a touch screen such that a user may input a target output pressure into the respirator through the button and/or the touch screen.

The control unit 52 may determine the rotating speeds of perspective blowers according to the target output pressure that is supplied by the input unit, and drive the corresponding blowers to rotate according to the determined rotating speeds. For example, the control unit is set to determine the rotating speeds of respective blowers corresponding to the current target output pressure through searching a comparison table or curve which is pre-stored and reflects the correspondence between the target output pressure and the rotating speeds of the respective blowers. Specifically, after the control unit 52 acquires the target output pressure that is supplied by the input unit, a pre-stored comparison table or curve may be searched according to the target output pressure to find out the blower rotating speeds corresponding to the target output pressure in the comparison table or curve, the searched blower rotating speeds are determined as the rotating speeds of the first blower 1 and/or the second blower 2, so the rotation of the first blower 1 and the second blower 2 may be controlled according to the searched rotating speeds; or, the rotation of each of the blowers may be respectively controlled according to the searched blower rotating speeds, for example the rotation of the first blower 1 may be controlled according to the rotating speed of the first blower 1, and/or the rotation of the second blower 2 may be controlled according to the rotating speed of the second blower 2, etc.

Optionally, the control system of the respirator may also include a monitoring unit 53 for monitoring the actual output pressure of the airflow output channel 4. Specifically, the control system may adopt the monitoring unit 53 to monitor the actual output pressure of the airflow channel 4 in the respirator, thus determining the output pressure of the airflow channel 4 in real time, then judging whether or not to adjust the rotating speeds of the first blower 1 and/or second blower on the basis of the determined output pressure, and ensuring that the rotating speeds of the first blower 1 and/or the second blower are within the preset ranges to meet the user demands.

The control system of the respirator may also include a display unit 54. The display unit 54 displays the actual output pressure provided by the monitoring unit, so the user conveniently acquires the deviation between the actual output pressure and the current target output pressure.

The comparison table or curve can be obtained by experimental means. The comparison table fails to exhaust the target output pressure. Therefore, on the one hand, the target output pressure input by the user can be limited, and the corresponding comparison table can be obtained through experiment means according to the limit; and on the other hand, user is allowed to input any target output pressure, which requires the control unit to be capable of determining the rotating speeds of the blowers by means of interpolation according to the comparison table.

In addition, the control unit 52 may also include control units corresponding to the blowers one by one. For example, in the embodiment in which the respirator includes one first blower 1 and one second blower 2, the control unit 52 may include a first control sub-unit and a second control sub-unit. In this embodiment, the first control sub-unit determines the rotating speed of the first blower 1 and drives the first blower 1 to rotate according to the determined rotating speed; the second control sub-unit determines the rotating speed of the second blower 2, and determines the rotation of the second blower 2 according to the determined rotating speed. The control sub-unit may not only be used to determine the rotating speeds of the corresponding blowers, but also drives the corresponding blowers according to the determined rotating speeds. This means that the respective control sub-units are pre-stored with a comparison table which reflects the corresponding relationship between the target output pressure and the rotating speeds of the corresponding blowers, and determine the rotating speeds of the corresponding blowers that correspond to the current target output pressure according to the respective comparison tables.

The monitoring unit 53 may include a flow sensor and/or a pressure sensor. The sensor(s) is specifically installed in the airflow output channel 4 to acquire the actual output pressure according to the acquired gas flow and/or gas pressure.

The respirator is affected by various factors in use, which may result in a deviation of the actual output pressure relative to the current target output pressure which is input by the user. Therefore, in a specific embodiment of the disclosure, the input unit 51 may receive the rotating speed adjusting request and supplies the rotating speed adjusting request to the control unit 52. The control unit 52 may also receive the rotating speed adjusting request supplied by the input unit 51, and adjusts the rotating speeds of the blowers according to the rotating speed adjusting request. In this embodiment, the rotating speed adjusting request may specifically include a rotating speed rise request and a rotating speed reduction request, wherein the rotating speed rise request may apply to enhancing the rotating speeds of the blowers, and the rotating speed reduction request may apply to reducing the rotating speeds of the blowers.

Specifically, when receiving the rotating speed rise request or the rotating speed reduction request which is triggered by the user, the input unit 51 may supply the received rotating speed rise request or the rotating speed reduction request to the control unit 52; correspondingly, the control unit 52 may raise the rotating speed of each one of the blowers by one adjusting step (the adjusting step is set upon demand) each time when receiving the rotating speed rise request and may reduce the rotating speed of each one of the blowers by one adjusting step each time when receiving the rotating speed reduction request. In this embodiment, the adjusting step may be used to control the rotation of each one of the blowers, for example representing a preset shift for controlling the running of the blowers.

Figure 12:
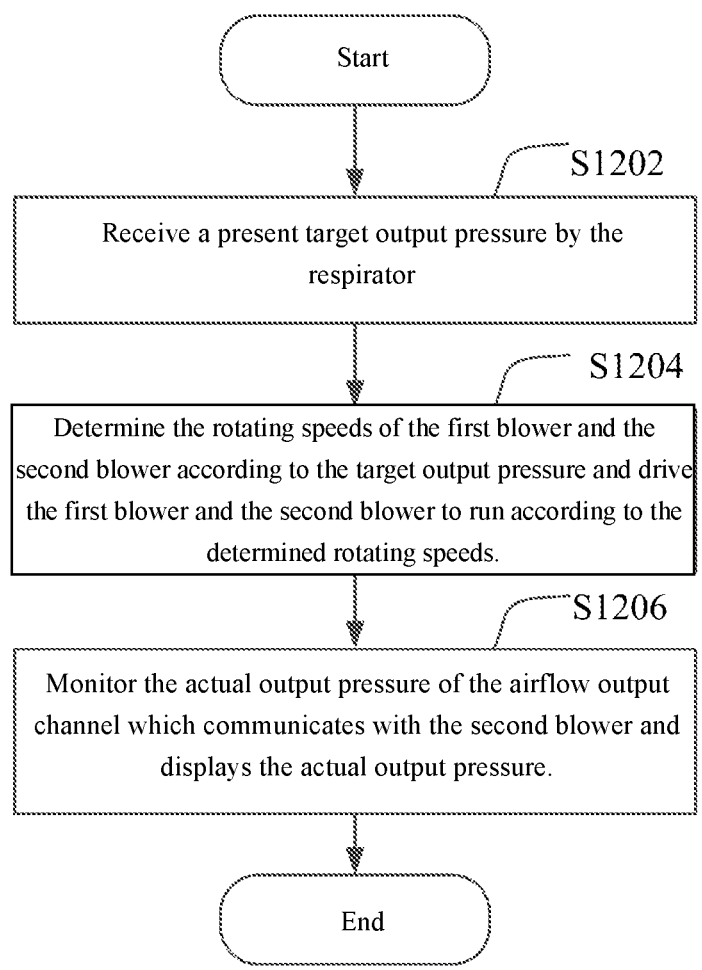
FIG. 12 is a flow chart of a method for processing the respirator according to one embodiment of the disclosure.

Refer to FIG. 12, which illustrates a flow chart of one embodiment of a method for processing the respirator according to the disclosure. The method for processing the respirator in the embodiments of the disclosure may specifically include the following steps:

S1202, receiving a present target output pressure by the respirator;

S1204, determining the rotating speeds of the first blower 1 and the second blower 2 according to the target output pressure, and driving the first blower and the second blower to run according to the determined rotating speeds.

The respirator in the embodiments of the disclosure may adopt determine the rotating speeds of the first blower 1 and the second blower 2 according to the received target output pressure, wherein the first blower 1 as an air supply source supplies air to the second blower 2 to obtain a two-level pressure boosting effect. Therefore, with respect to the existing respirators, the respirator of the disclosure may lower requirements for the rotating speeds of the blowers under the condition of the same target output pressure, and then the respirator of the disclosure has higher performance in the aspects of response speed, noise reduction, heat value, etc.

In a specific embodiment of the disclosure, optionally, the method for processing the respirator may also include: Step 1206, monitoring the actual output pressure of the airflow output channel which communicates with the second blower, and displaying the actual output pressure.

In a specific embodiment of the disclosure, optionally, the method for processing the respirator may also include receiving a rotating speed adjusting request by the respirator, and adjusting the rotating speeds of the blowers according to the rotating speed adjusting request, wherein the blowers include first blower 1 and second blower 2. Specifically, the respirator receives the rotating speed rise request or the rotating speed reduction request which is triggered by the user; the rotating speed of each one of the blowers is raised by one adjusting step each time when the rotating speed rise request is received; or, the rotating speed of each one of the blower is reduced by one adjusting step each time when the rotating speed reduction request is received, wherein the first blowers include the first blower and the second blower.

The disclosure may also be configured as computer program products of a computer readable storage media, including computer program codes. When the computer program codes are executed by the processor, the processor can realize the method for processing the respirator described in the embodiments in the text according to the method of the embodiments of the disclosure. The computer storage medium may be any physical media, for example, floppy disk, CD-ROM, DVD, hard disc drive or even network media, etc.

Figure 13:
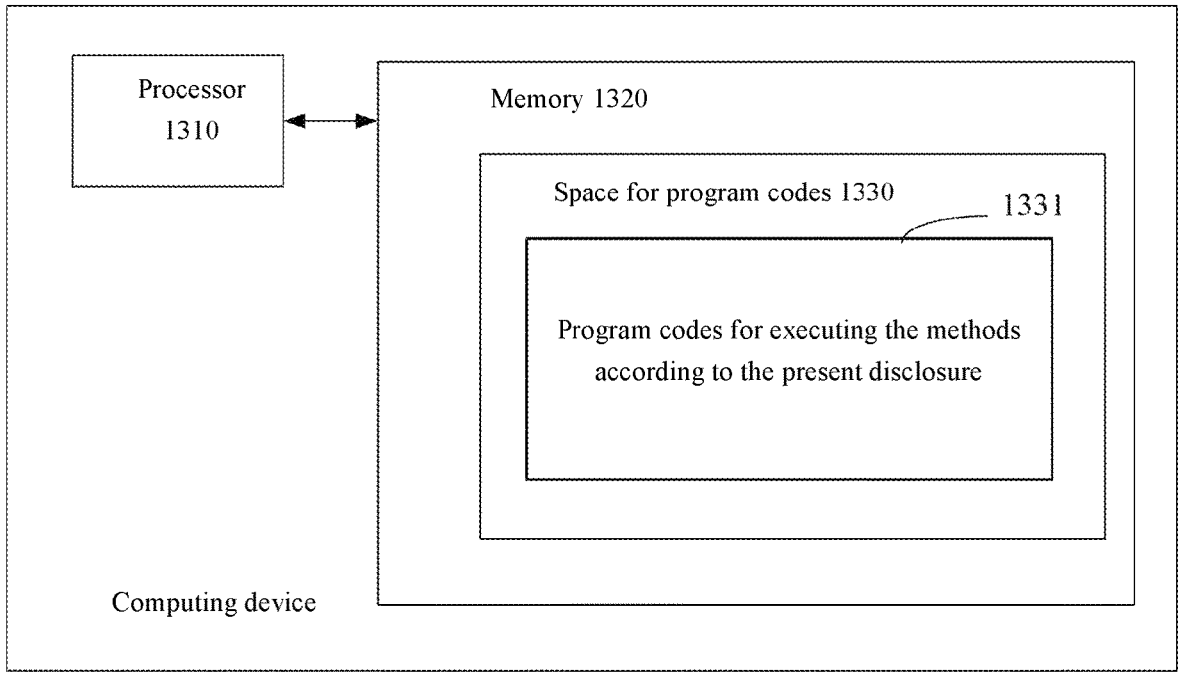
FIG. 13 illustrates a block diagram of a computing device which may realize the control over the rotation of all blowers according to a target output pressure input by a user according to the disclosure.
Figure 14:
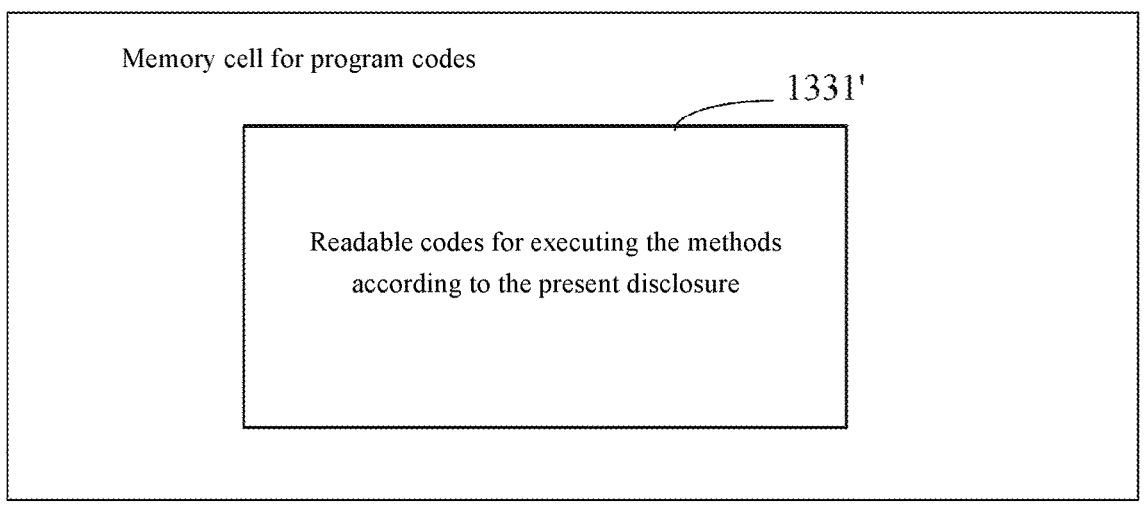
FIG. 14 illustrates a memory cell for keeping or carrying program codes of the control method which may realize the control over the rotation of all blowers according to a target output pressure input by a user according to the disclosure.

For example, FIG. 13 illustrates a computing device for executing the method for processing the respirator according to the disclosure. For example, the computing device may include cloud platform devices, a server, respirator devices, etc. Traditionally, the computing device includes a processor 1310 and a computer program product or a computer readable medium in the form of a memory 1320. For example, the processor may include processing units of the respirator. The memory 1320 could be electronic memories such as flash memory, EEPROM (Electrically Erasable Programmable Read-Only Memory), EPROM or ROM, for example the storage device of the respirator. The memory 1320 has a memory space 1330 for executing program codes 1331 of any steps in the method of the control system of the control method. For example, the storage space 1330 for program codes can include the program codes 1331 for respectively executing all steps of the above methods. The programs can be read from one or more program products or written into one or more program products. The program products include program code carriers such as memory cards. Such program products are usually portable or fixed storage units as shown in FIG. 14. The storage units can have storage segments, storage space, etc. similar to the memories 1320 in the computer device as shown in FIG. 13 The program codes can be compressed in a proper form. Usually, the memory cell includes computer readable codes 1331 which can be read for example by processors 1310. When these codes are operated on the computing device, the computing device may execute respective steps in the method as described above.

It should also be understood that, the flow chart in FIG. 12 and the block diagram of FIG. 11 illustrate the functions and operations of possible realization of the method or computer program product in all embodiments of the disclosure. Every square block in the flow chart and block diagram may represent a module, a program segment or a code section, wherein the module, the program section or the code section includes one or more executable instructions for realizing the pre-set logic functions. It should also be noted that, in some alternative realizations, the functions marked in the square blocks may be executed in a sequence different from that marked in the drawings. For example, two consecutive square blocks actually may be basically executed in parallel or executed in a reverse sequence which depends on the functions involved. For example, step S1202 and step S1204 as well as the step S1206 may be executed in different sequences. When the actual output pressure of the airflow output channel is monitored, the monitoring and display functions of the step S1206 are conducted in real time; only when the respirator receives a pre-set target output pressure, can step S1202 and step S1204 be executed to perform real-time control over the first blower and the second blower.

It should also be noted that the contents in every square block of the block diagram and the contents of the combinations of the square blocks of the block diagram and/or flow chart can be realized with a special hardware-based system for executing specific functions or operations, or realized with combinations of special hardware and computer instructions.

In various embodiments of the disclosure, the respirator of the disclosure adopts a power structure which includes the first blower and the second blower wherein the first blower as an air supply source supplies air to the second blower to obtain a secondary pressure boosting effect. Therefore, with respect to the existing respirators (which adopt a single-blower power structure), the respirator of the disclosure may lower the requirements for the rotating speeds of the blowers under the condition of the same target output pressure, and then the respirator of the disclosure has a higher performance in the aspects of response speed, noise reduction, heat value, air supply, etc.

The description of the disclosure is given for the purposes of disclosure and depiction, but does not aim to exhaust or limit the invention in the disclosed form. Those skilled in the art can conceive of many modifications and changes after reading the contents of the present disclosure. All embodiments described above can be used individually or in combination, unless otherwise clearly specified in the context.

All embodiments in this Description are all described in a progressive way. The identical and similar parts of all the embodiments may be used as a reference for each one. The focus of each one of the embodiments is different, and the embodiments can be used individually or combined upon demand.

Some specific embodiments of the disclosure are detailed through examples, but those skilled in the art should understand that the above examples are only illustrating instead of limiting the scope of the disclosure. Those skilled in this field shall understand that the embodiments above may be modified without departing from the spirit of the present invention. The scope of the disclosure is defined by the claims and equivalents thereof.

What is claimed is:

1. A respirator, comprising a plurality of blowers and an airflow output channel which communicates with the corresponding one of the plurality of blowers, wherein the plurality of blowers includes a first blower and at least one second blower; an air inlet of the at least one second blower is configured to communicate with an air outlet of the first blower, a control system, and an air outlet of the at least one second blower is configured to communicate with the airflow output channel;
   wherein each of the first blower and the at least one second blower is independently controllable relative to the other, the first blower comprises a first housing:
   wherein the control system comprises: an input unit, configured to receive a target output pressure; and a control unit, configured to determine a rotating speed for the first blower and a rotating speed for the at least one second blower according to the target output pressure provided by the input unit and based on comparison tables or curves, respectively; wherein the control unit drives the first blower and the at least one second blower to run according to each of the determined rotating speeds, respectively.

2. The respirator according to claim 1, wherein the respirator further comprises a sealing housing which is located on the exterior of the at least one second blower and encloses the at least one second blower, and a space is formed between the sealing housing and the at least one second blower to form a heat dissipating cavity for air flow; the air outlet of the first blower communicates with a cavity inlet of the heat dissipating cavity, and the air inlet of the at least one second blower communicates with the air outlet of the first blower through the cavity inlet.

3. The respirator according to claim 2, wherein a central line of the air inlet of the at least one second blower is not super-imposed with a central line of the cavity inlet of the heat dissipating cavity.

4. The respirator according to claim 1, wherein the air inlet of the at least one second blower communicates with the air outlet of the first blower through a sealing pipe.

5. The respirator according to claim 4, wherein each of: a first sealing connection between the sealing pipe and the air inlet of the at least one second blower, and a second sealing connection between the sealing pipe and the air outlet of the first blower is achieved through a sealing ring, a sealing rubber, a sealing gasket, or the sealing pipe; and wherein the air inlet of the at least one second blower, and the sealing pipe and the air outlet of the first blower are complementarily shaped so that each of the sealing pipe ends matingly fits with a corresponding air outlet or air inlet, respectively.

6. The respirator according to claim 1, wherein the first blower and the at least one second blower are connected in an air-fight fashion by an elastic sealing bag and the first blower and the at least one second blower are secured in a blower fixing cabin.

7. The respirator according to claim 1, wherein the first blower and the at least one second blower are configured in a one-to-one correspondence way; the air outlet of the first blower is in a sealing connection with the air inlet of the at least one second blower through an elastic sealing bag, wherein the first blower and the at least one second blower are enclosed in the elastic sealing bag, the air outlet of the first blower and the air inlet of the at least one second blower communicate with each other in each corresponding elastic sealing bag, and the air inlet of the first blower and the air outlet of the at least one second blower are exposed through each corresponding elastic sealing bag.

8. The control system according to claim 1, wherein the control system further comprises:
   a monitoring unit configured to monitor an actual output pressure of the airflow output channel in the respirator.

9. The control system according to claim 8, wherein the control system further comprises:
   a display unit, configured to display the actual output pressure provided by the monitoring unit.

10. The control system according to claim 1, wherein the input unit is further configured to receive a rotating speed adjusting request, and send the rotating speed adjusting requests to the control unit, wherein the rotating speed adjusting request comprises a rotating speed rise request or a rotating speed reduction request;
    the control unit is further configured to receive the rotating speed adjusting request provided by the input unit and adjust the rotating speeds of the blowers according to the rotating speed adjusting requests.

11. The control system according to claim 1, wherein the control unit comprises:
    a first control sub-unit, configured to determine the rotating speed of the first blower and drive the first blower to run according to the determined rotating speed of the first blower;
    a second control sub-unit, configured to determine the rotating speed of the at least one second blower and drive the at least one second blower to run according to the determined rotating speed of the at least one second blower.

12. A method for operating a respirator, wherein the respirator is the respirator according to claim 1; the method comprising:
    receiving a target output pressure by the input unit;
    determining rotating speeds of the first blower and the at least one second blower according to the target output pressure, and driving the first blower and the at least one second blower to run according to the determined rotating speeds, respectively.

13. The method according to claim 12, wherein the method further comprises:
- monitoring an actual output pressure of the airflow output channel which communicates with the at least one second blower, and displaying the actual output pressure.

14. The method according to claim 12, wherein the method further comprises:
- receiving a rotating speed adjusting request by the input unit;
- adjusting the rotating speeds of the blowers according to the rotating speed adjusting request, wherein the blowers include the first blower and the at least one second blower.

15. The method according to claim 14, wherein the rotating speed adjusting request comprises a rotating speed rise request or a rotating speed reduction request;
- wherein the step of adjusting the rotating speeds of the blowers according to the rotating speed adjusting request comprises:
- increasing the rotating speed of each one of the blowers by an adjusting step each time when receiving the rotating speed rise request; or
- reducing the rotating speed of each one of the blowers by an adjusting step each time when receiving the rotating speed reduction request; and
- wherein said rotating speed adjusting request is made based on an actual output pressure of the airflow channel that communicates with the at least one second blower.

* * * * *